United States Patent [19]

Makinson et al.

[11] 4,116,998

[45] Sep. 26, 1978

[54] PREPARATION OF ESTERS OF M-PHENOXYBENZYL ALCOHOL AND ITS α-CYANO AND α-ETHINYL DERIVATIVES WITH 2,2-DIMETHYLCYCLOPROPANECARBOXYLIC ACIDS

[75] Inventors: George Kenneth Makinson; David Schofield, both of Manchester, England

[73] Assignee: Imperial Chemical Industries Limited, London, England

[21] Appl. No.: 784,635

[22] Filed: Apr. 4, 1977

[30] Foreign Application Priority Data

Apr. 15, 1976 [GB] United Kingdom ............... 15583/76

[51] Int. Cl.$^2$ ........................................... C07B 121/66
[52] U.S. Cl. ................................. 260/465 D; 560/124; 560/105
[58] Field of Search ................... 260/465 D; 560/124, 560/105

[56] References Cited

U.S. PATENT DOCUMENTS

| 3,666,789 | 5/1972 | Itaya et al. | 560/124 |
| 3,795,696 | 3/1974 | Katsuda et al. | 560/124 |
| 3,943,167 | 3/1976 | Suzukamo et al. | 560/124 |
| 3,973,036 | 8/1976 | Hirano et al. | 560/124 |
| 4,024,163 | 5/1977 | Elliott et al. | 560/124 |

OTHER PUBLICATIONS

Kato et al., Chemical Abstracts 79: 31609k (1973).

*Primary Examiner*—Lewis Gotts
*Assistant Examiner*—Molly C. Eakin
*Attorney, Agent, or Firm*—Cushman, Darby & Cushman

[57] ABSTRACT

Process for the preparation of esters of m-phenoxybenzyl alcohol and its α-cyano and α-ethinyl derivatives with carboxylic acids containing at least 6 carbon atoms by heating together a methyl or ethyl ester of the carboxylic acid, an ester of m-phenoxyphenyl alcohol or its α-cyano or α-ethinyl derivative with an acid of the formula $R.CO_2H$ wherein R is an alkyl group containing not more than 3 carbon atoms, and tetramethyl or tetraethyl titanate at a temperature such that the methyl or ethyl ester of the acid of formula $R.CO_2H$ is removed by distillation as it is formed.

9 Claims, No Drawings

PREPARATION OF ESTERS OF M-PHENOXYBENZYL ALCOHOL AND ITS α-CYANO AND α-ETHINYL DERIVATIVES WITH 2,2-DIMETHYLCYCLOPROPANECARBOXYLIC ACIDS

This invention relates to an improved process for the manufacture of esters of m-phenoxybenzyl alcohol.

A number of esters of m-phenoxybenzyl alcohol are of insecticidal value, for example those with certain substituted 2,2-dimethylcyclopropanecarboxylic acids. Our copending Application Ser. No. 784,636, filed Apr. 4, 1977 describes a process for the preparation of esters of m-phenoxybenzyl alcohols by heating the alcohol with methyl or ethyl esters of these or other carboxylic acids with tetramethyl or tetraethyl titanate.

It has now been found that in the above process the m-phenoxybenzyl alcohols may be replaced, in some cases with advantage, by the corresponding esters with certain organic acids.

According to the invention there is provided a process for preparing esters of m-phenoxybenzyl alcohol and its α-cyano and α-ethinyl derivatives with carboxylic acids containing at least 6 carbon atoms which comprises mixing a methyl or ethyl ester of the carboxylic acid, an ester of m-phenoxybenzyl alcohol or its α-cyano or α-ethinyl derivative with an acid of formula $R.CO_2H$ wherein R is an alkyl group containing not more than 3 carbon atoms, and tetramethyl or tetraethyl titanate and heating the mixture at a temperature such that the methyl or ethyl ester of the acid of formula $RCO_2H$ is removed by distillation as it is formed.

The ingredients of the process may be mixed in any order and the mixture, preferably stirred or otherwise agitated, raised to reaction temperature. The preferred reaction temperatures are between 70° C. and 160° C. Temperatures outside this range may be used but lower temperatures may necessitate prolonged reaction times and higher temperatures involve a risk of decomposition of the product.

If desired a solvent may also be used especially one which gives a reaction mix boiling at the desired reaction temperature so that the methyl or ethyl ester of the acid $R.CO_2H$ formed during the process is distilled off with a part of the solvent.

Suitable solvents are hydrocarbons such as toluene or methylcyclohexane halogenated hydrocarbons wherein the halogen atom is inert under the reaction conditions, e.g. chlorinated aromatic hydrocarbons such as chlorobenzene, and ethers such as dioxan. Lower boiling solvents such as cyclohexane may be used but need a longer reaction period at atmospheric pressure. The solvent and other ingredients of the reaction mixture should be free from water. As acids of formula $R.CO_2H$, m-phenoxybenzyl esters of which are used in the process of the invention, there are mentioned propionic and butyric, but especially acetic acids.

Titanate esters of higher alcohols, e.g. tetrabutyl titanate, are also effective catalysts of the process, but tend to form titanium compounds with the m-phenoxybenzyl alcohol with consequent lower yield and lower purity of the desired product.

The ester, e.g. acetate, of the m-phenoxybenzyl alcohol or α-cyano or α-ethinyl derivative thereof, may be obtained by any conventional method, for example reaction of the free benzyl alcohol with an acid chloride or anhydride.

The amount of methyl or ethyl titanate is at least 0.02 mol and preferably from 0.05 to 0.2 mol per mol of methyl or ethyl ester of carboxylic acid.

The required proportions of ester of m-phenoxybenzyl alcohol or its α-cyano or α-ethinyl derivative and methyl or ethyl ester of carboxylic acid containing at least 6 carbon atoms are equimolar. Excess of either reactant may be used if desired and may generally be recovered unreacted at the end of the process.

The ester produced by the process of the invention may be isolated by any convenient procedure, for example by removing the solvent, if any, and any unchanged reactant, by distillation to leave the crude ester which could be purified by conventional means suitable for the ester concerned.

The methyl or ethyl ester of a carboxylic acid which may be used in the process of the invention may be derived from any aliphatic, aromatic, cycloaliphatic or heterocyclic carboxylic acid containing at least 6 carbon atoms but the process of the invention is of particular value for the manufacture of m-phenoxybenzyl, α-cyano and α-ethinyl-m-phenoxybenzyl esters of insecticidal activity, for example from 4-methyl-α-isopropylphenylacetic acid or more especially of pyrethrin-type esters of 2,2-dimethylcyclopropanecarboxylic acids.

Examples of these are particularly esters of 2,2-dimethylcyclopropanecarboxylic acids containing in the 3-position substituted vinyl groups such as 2',2'-dimethylvinyl, 2',2'-dichlorovinyl, 2'-ethylvinyl and 2',2'-dibromovinyl. These acids are normally obtained as mixtures of cis and trans forms, which in the case of the derived m-phenoxybenzyl esters have different insecticidal potency. The process of the invention is particularly valuable in that it brings about a minimum of interconversion of the cis into the less potent trans forms. Also in those cases where the free alcohol is of low thermal stability, as for example with α-cyano-m-phenoxybenzylalcohol, use of the alcohol in the form of an ester as in the present process affords higher yields of products.

The invention is illustrated but not limited by the following Examples in which all parts and percentages are by weight unless otherwise stated.

EXAMPLE 1

A solution of 24.2 parts of m-phenoxybenzyl acetate, 28.4 parts of ethyl 2,2-dimethyl-3-(2'-,2'-dichlorovinyl)-cyclopropanecarboxylate (cis:trans ratio, 58/42) and 1.3 parts of tetraethyl titanate in 200 parts of dry toluene was stirred and heated at the boiling point. The azeotrope of ethyl acetate and toluene was removed by distillation at the rate of 50 parts per hour while maintaining the reaction volume by the addition of fresh toluene. After 4 hours 5 parts of water were added and precipitated titanium dioxide removed by filtration. The toluene was then removed by heating under reduced pressure and 0.3 mm. of mercury. Volatile fractions removed were 9.0 parts of unreacted ethyl 2,2-dimethyl-3-(2',2'-dichlorovinyl)cyclopropanecarboxylate, boiling at 75°–80° and 6.3 parts of unchanged m-phenoxybenzyl acetate, boiling at 125°–135°. There was obtained 26.85 parts of m-phenoxybenzyl 2,2-dimethyl-3-(2',2'-dichlorovinyl)-cyclopropanecarboxylate (cis trans ratio, 44/56).

EXAMPLE 2

A mixture of 121 parts of m-phenoxybenzyl acetate, 142 parts of ethyl 2,2-dimethyl-3-(2',2'-dichlorovinyl)-cycloproanecarboxylate (cis-trans ratio 58:42) and 6.45 parts of tetramethyl titanate in 950 parts of toluene was heated at the boiling point while removing ethyl acetate/toluene azeotrope at a rate of about 135 parts an hour. After 4 hours 2 parts of water were added and precipitated titanium dioxide separated by filtration, and the residue heated to remove toluene and, under reduced pressure, 42 parts of unreacted ethyl 2,2-dimethyl-3-(2',2'-dichlorovinyl)cyclopropanecarboxylate, 30 parts of m-phenoxybenzyl acetate and, residue, 144 parts of m-phenoxybenzyl 2,2-dimethyl-3-(2',2'-dichlorovinyl) cyclopropanecarboxylate (cis-trans ratio, 53:47).

What we claim is:

1. A process for preparing insecticidal esters of m-phenoxybenzyl alcohol and its α-cyano and α-ethinyl derivatives with a 2,2-dimethylcyclopropanecarboxylic acid which comprises mixing a methyl or ethyl ester of the carboxylic acid, an ester of m-phenoxybenzyl alcohol or its α-cyano or α-ethinyl derivative with an acid of formula $R.CO_2H$ wherein R is an alkyl group containing not more than 3 carbon atoms, and tetramethyl or tetraethyl titanate and heating the mixture at a temperature such that the methyl or ethyl ester of the acid formula $RCO_2H$ is removed by distillation as it is formed.

2. A process as claimed in claim 1 wherein the reaction temperature is between 70° and 160° C.

3. A process as claimed in claim 1 wherein the process is carried out in an anhydrous solvent.

4. A process as claimed in claim 3 wherein the solvent is such that it gives a reaction mixture boiling at the desired reaction temperature, whereby the methanol or ethanol formed is distilled off with a part of the solvent.

5. A process as claimed in claim 1 wherein the acid of formula $R.CO_2H$ is acetic acid.

6. A process as claimed in claim 1 wherein the amount of methyl or ethyl titanate is at least 0.02 mol per mol of methyl or ethyl ester of the carboxylic acid.

7. A process as claimed in claim 1 wherein the amount of methyl or ethyl titanate is from 0.05 to 0.2 mol per mol of methyl or ethyl ester of the carboxylic acid.

8. A process as claimed in claim 1 wherein the ester of m-phenoxybenzyl alcohol or its α-cyano or α-ethinyl derivative and the methyl or ethyl ester of the 2,2-dimethylcyclopropanecarboxylic acid are employed in equimolar proportions.

9. A process as claimed in claim 1 wherein the 2,2-dimethylcyclopropanecarboxylic acid contains a 2',2'-dimethylvinyl, 2',2'-dichlorovinyl, 2'-ethylvinyl or 2',2'-dibromovinyl group in the 3-position.

* * * * *